Figure 1:
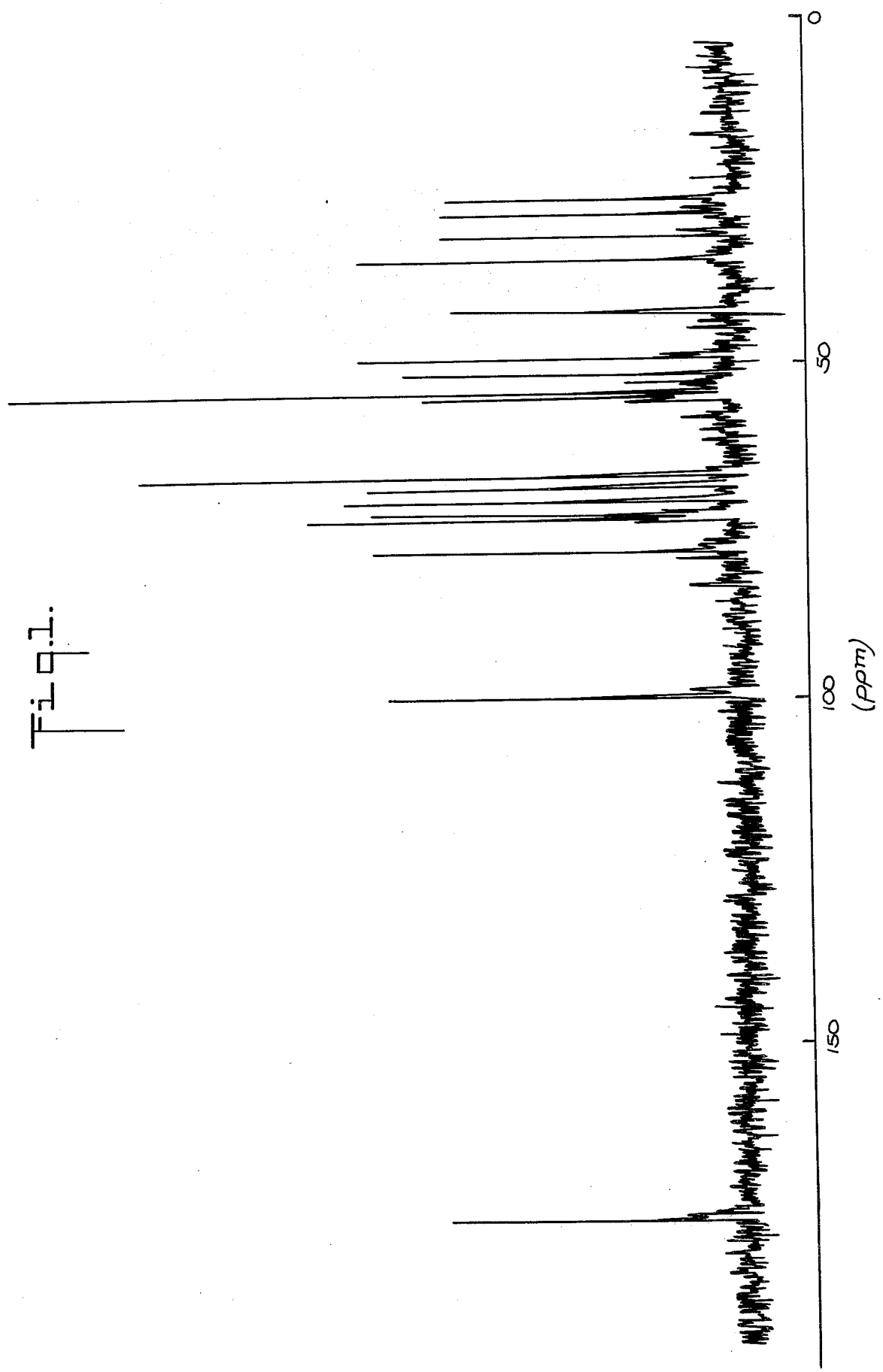

| United States Patent [19] | [11] | 4,169,942 |
|---|---|---|
| Mochida et al. | [45] | Oct. 2, 1979 |

[54] FORTIMICIN DERIVATIVES AND METHOD FOR PRODUCTION THEREOF

[75] Inventors: Kenichi Mochida, Hiratsuka; Yasuki Mori, Kawasaki, both of Japan

[73] Assignee: Abbott Laboratories, North Chicago, Ill.

[21] Appl. No.: 899,725

[22] Filed: Apr. 25, 1978

[30] Foreign Application Priority Data

May 11, 1977 [JP] Japan .................................. 52-53879

[51] Int. Cl.$^2$ ............................................ C07H 15/22
[52] U.S. Cl. .................................. 536/17 R; 424/180;
424/181; 536/4; 536/10; 536/12
[58] Field of Search ............................... 536/10, 17, 12

[56] References Cited

U.S. PATENT DOCUMENTS

| 3,350,387 | 10/1967 | Vanderhaeghe | 536/10 |
|---|---|---|---|
| 3,925,353 | 12/1975 | Umezawa et al. | 536/17 |
| 3,931,400 | 1/1976 | Nara et al. | 424/118 |
| 3,997,524 | 12/1976 | Nagabhushan | 536/17 |
| 4,044,123 | 8/1977 | Daniels et al. | 536/17 |
| 4,048,430 | 9/1977 | Cooper et al. | 536/17 |
| 4,063,015 | 12/1977 | Mallams | 536/17 |
| 4,124,756 | 11/1978 | Martin et al. | 536/17 |

*Primary Examiner*—Johnnie R. Brown
*Attorney, Agent, or Firm*—Fitzpatrick, Cella, Harper & Scinto

[57] ABSTRACT

6'-N-methylfortimicin D and 6'-N-methylfortimicin KE are produced by chemically moidifying fortimicin KE. 6'-N-methylfortimicin D is useful as an antibacterial compound; and 6'-N-methylfortimicin KE is useful as an intermediate in the synthesis of the former compound.

4 Claims, 2 Drawing Figures

FORTIMICIN DERIVATIVES AND METHOD FOR PRODUCTION THEREOF

BACKGROUND OF THE INVENTION

The present invention relates to new fortimicin derivatives represented by the general formula I:

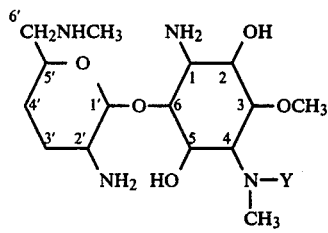

wherein Y is H or —COCH$_2$NH$_2$; and when Y is H, the derivative is 6'-N-methylfortimicin KE; and when Y is —COCH$_2$NH$_2$, the derivative is 6'-N-methylfortimicin D. Fortimicin KE and fortimicin D are known pseudodisaccharride antibiotics having a 1,4-diamanocyclitol moiety. The compounds and processes for production thereof are described an Japanese Patent Application Nos. 128837/76 and 2338/77, and U.S. patent application Ser. No. 845,970 filed on Oct. 27, 1977. Although these compounds have antibacterial activity, compounds having a more pronounced activity are in demand. To this end, it has now been found that 6'-N-methylfortimicin D in which the amino group at the 6'-position of fortimicin D is methylated has a stronger antibacterial activity than the parent compound.

SUMMARY OF THE INVENTION

In accordance with the present invention, 6'-N-methylfortimicin KE and 6'-N-methylfortimicin D are synthetically produced by the following general conversion steps:

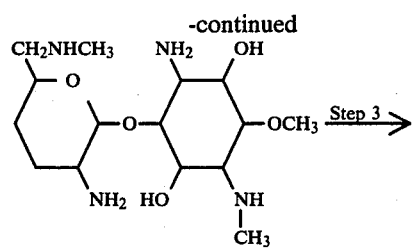

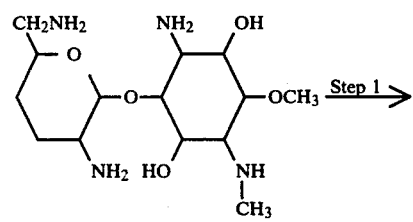

fortimicin KE

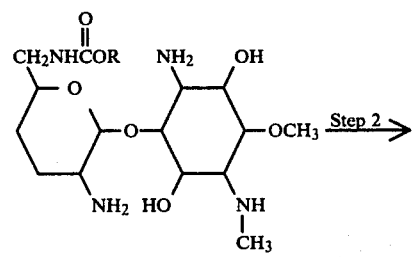

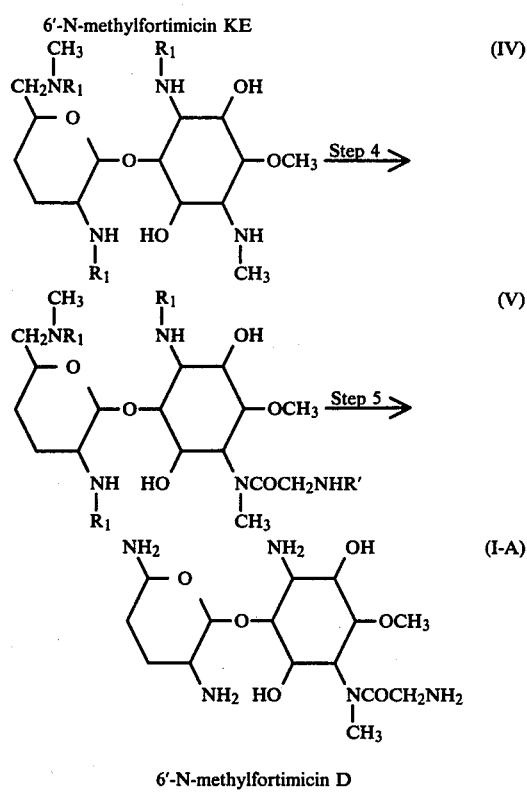

6'-N-methylfortimicin D wherein R is an alkyl group having 1 to 7 carbon atoms or an aralkyl group having 7 or 8 carbon atoms and R$_1$ and R' are an amino-protecting group such as

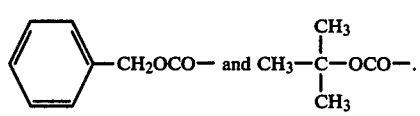

6'-N-methylfortimicin D exhibits a broad spectrum of antibacterial activity and is, therefore, usuful inter alia to clean and sterilize laboratory glassware and surgical instruments, and may also be used in combination with soaps, detergents and wash solutions for sanitation purposes. On the other hand, 6'-N-methylfortimicin KE is useful as an intermediate in the production of 6'-N-methylfortimicin D.

Included in the composition of matter aspect of the invention are the pharmaceutically acceptable non-toxic acid addition salts of 6'-N-methylfortimicin D including the mineral acid addition salts such as hydrochloride, hydrobromide, hydroiodide, sulfate, sulfamate and phosphate and the organic acid salts such as maleate, acetate, citrate, oxalate, succinate, benzoate, tartrate, fumarate, malate, mandelate, ascorbate and the like.

DESCRIPTION OF THE INVENTION

6'-N-methylfortimicin D represented by the formula I-A:

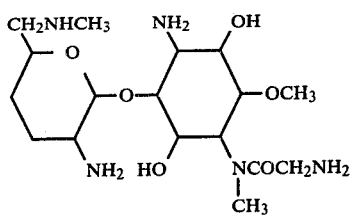

and 6'-N-methylfortimicin KE represented by the formula I-B:

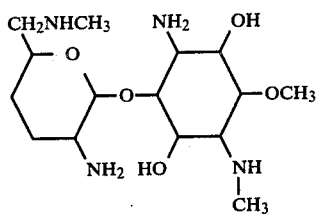

are novel compounds having the following physicochemical properties.

6'-N-methylfortimicin D (1) White powder (2) In thin layer chromatography using the lower layer of chloroform, methanol, and concentrated aqueous ammonia (1:1:1 by volume) as the developer, the Rf value is 0.47.

(3) NMR spectrum (proton) δ(ppm):
 a. The free base (in $D_2O$): 2.31 (3H, s), 3.02 (3H, s), 3.40 (3H, s), 3.47 (2H, s), 4.75 (1H, d).
 b. The hydrochloride (a sample wherein DCl is added to the free base to make pD=1 was used): 2.77 (3H, s), 3.12 (3H, s), 3.47 (3H, s), 4.06 (2H, s), 5.32 (1H, d).

(4) Mass spectrum (m/e): 405 ($M^+$), 387, 356, 292, 274, 264, 246, 207, 143

(5) Melting point (free base): 88°–91° C.

(6) Specific rotation (sulfate)
 $[\alpha]_D^{22} = +82.0°$ (c=0.2, $H_2O$)

Figure 2:
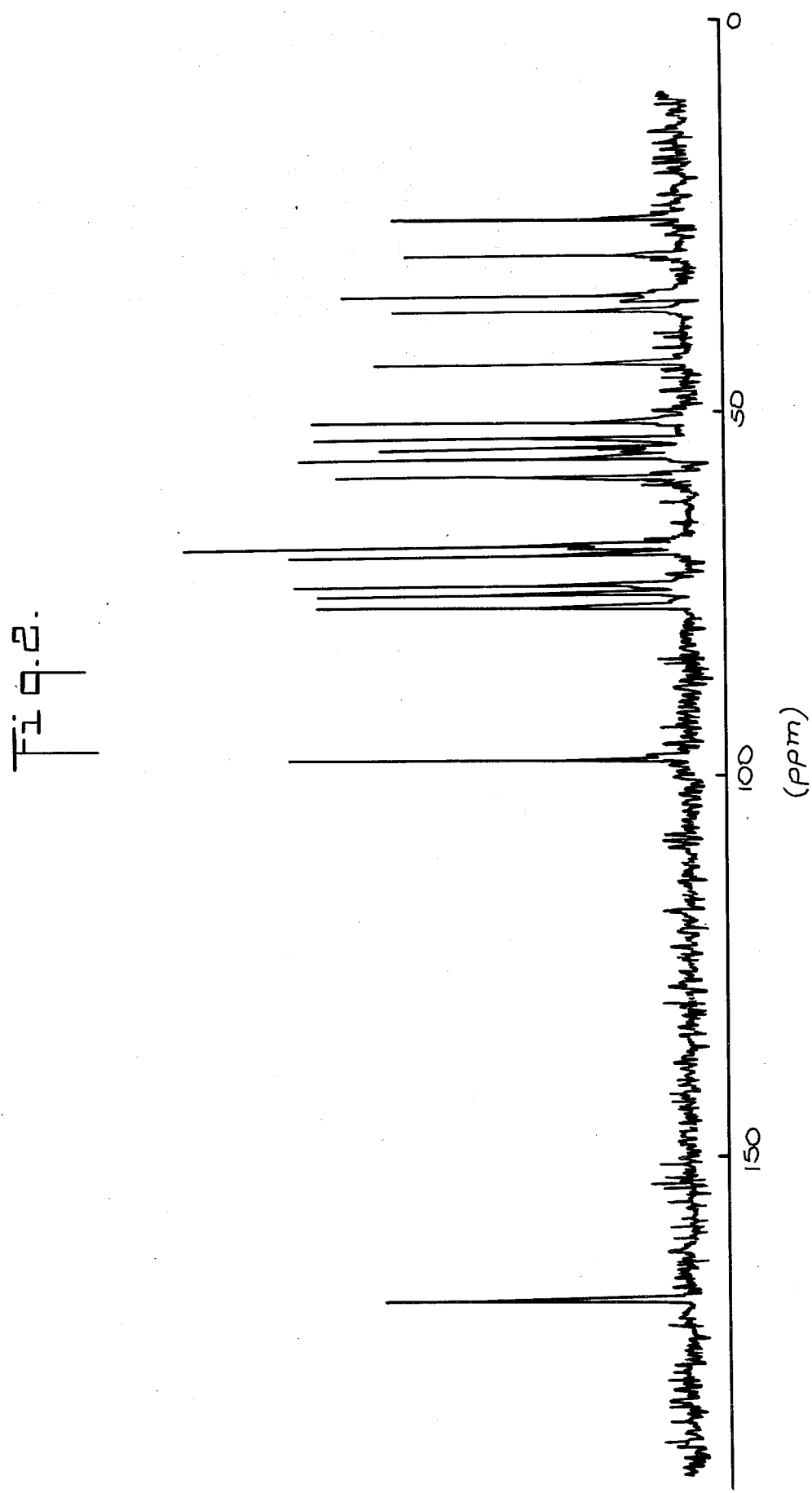

(7) CMR spectrum (dioxane was used as an internal standard); illustrated in FIGS. 1 and 2

| Elementary analysis $C_{17}H_{35}N_5O_6 \cdot 6.2O$ | | | |
|---|---|---|---|
| | H | C | N |
| Found | 8.79 | 49.00 | 16.63% |
| Calculated | 8.75 | 49.26 | 16.89% |

(9) Antibacterial activity (MIC, mcg/ml) determined by using a medium of pH 7.2 according to "the Japanese Antibiotic Medicament Standard" as shown in Table 1.

Table 1

| Microorganisms | fortimicin D | 6'-N-methyl-fortimicin D | Kanamycin |
|---|---|---|---|
| Staphylococcus aureus 209-P | 1.56 | 1.56 | 0.4 |
| Staphylococcus auteus Smith(A) | 1.56 | 3.12 | 0.4 |
| Staphylococcus aureus 226 | 3.12 | 6.25 | 0.78 |
| Escherichia coli NIHJC-2 | 6.25 | 6.25 | 1.56 |
| Escherichia coli KY-8371 | 25 | 3.12 | 3.12 |
| Escherichia coli | 6.25 | 6.25 | 3.12 |
| Klebsiella pneumoniae KY 4274 | 3.12 | 3.12 | <100 |
| Proteus vulgaris JJ | 25 | 6.25 | 1.56 |
| Salmonella enteritidis G-14 | 25 | 12.5 | 3.12 |
| Shigella sonnei ATCC 9290 | 12.5 | 6.25 | 3.12 |
| Pseudomonas aeruginosa BMH#1 | 25 | 12.5 | 25 |
| Escherichi coli 76-2 *1 | 6.25 | 6.25 | <100 |
| Escherichia coli 57R *1 | 6.25 | 6.25 | <100 |
| Escherichia coli KY 8321 *2 | 12.5 | 12.5 | <100 |
| Escherichia coli Z-343 *3 | 6.25 | 3.12 | 12.5 |
| Escherichia coli KY 8349 *4 | 3.12 | 3.12 | <100 |
| Providencia sp. 164 *5 | 100 | 25 | <100 |
| Serratia marcescens 1065 *3 | 12.5 | 6.25 | 100 |
| Klebsiella pneumoniae 3020 Y-60 | *1 25 | 25 | <100 |

*1 : producing 2''-adenylyltransferase
*2 : producing 2''-adenylyltransferase and 6'-acetyltransferase
*3 : producing 6'-acetyltransferase
*4 : producing 3'-phosphotransferase
*5 : producing 2'-acetyltransferase

6'-N-methylfortimicin KE (1) White powder (2) In thin layer chromatography using the lower layer of chloroform, methanol, and concentrated aqueous ammonia (1:1:1 by volume) as the developer, the Rf value is 0.72.

(3) NMR spectrum (in $D_2O$) δ(ppm): 2.38 (3H, s), 2.68 (3H, s), 3.47 (3H, s), 5.02 (1H, d)

(4) Mass spectrum (m/e): 348 ($M^+$), 331, 299, 258, 235, 217, 207, 189, 143, 114, 100, 86.

(5) Melting point: 86°–90° C.

| Elementary analysis $C_{15}H_{32}N_4O_5 \cdot CO_2$ | | | |
|---|---|---|---|
| | H | C | N |
| Found | 8.52 | 48.85 | 14.49% |
| Calculated | 8.22 | 48.97 | 14.28% |

Fortimicin KE, the starting material for the processes of the invention, is obtained by fermentation of a microorganism belonging to the species *Micromonospora olivoasterospora*, for example, *Micromonospora olivoasterospora* MK-70 (FERM-P 1560, ATCC 21819). The microbiological properties of suitable strains are described in U.S. Pat. No. 3,931,400, description of which is incorporated herein as reference. As stated above, fortimicin KE and the fermentative production thereof are described in U.S. patent application Ser. No. 845,970 filed on Oct. 27, 1977. Briefly, from a culture liquor obtained by fermentation of a suitable strain, fortimicin KE is obtained by the following way.

The filtrate of the culture liquor is adjusted to a pH of 7.5 and passed through a column packed with a cation exchange resin, such as Amberlite IRC-50 (ammonium form) (Rohm & Haas Co.). After washing the column with water, elution is carried out with 0.5 N aqueous ammonia. Biologically active fractions eluted are concentrated under reduced pressure and are subjected to an anion exchange resin chromatography using, for example, Dowex 1×2 (OH form) (The Dow Chemical Co.). Active fractions eluted are combined and concentrated under reduced pressure to obtain a crude powder of the fortimicin complex containing fortimicin A, fortimicin B, fortimicin C, fortimicin D and fortimicin KE. The crude powder is dissolved in water and adjusted to a pH of 5.0 with 2 N-sulfuric acid. The solution is passed through a column packed with active carbon to adsorb the active substances thereon. Impurities which are not adsorbed on the active carbon are eluted out by washing with water. Thereafter, 0.2 N-sulfuric acid is passed through the column to elute out active substances. Active fractions are combined and neutralized by passing through an anion exchange resin, such as Dowex 44 (OH form) (The Dow Chemical Co.). The eluate is freeze-dried to obtain the free base of a mixture of all components of the fortimicin complex.

The freeze-dried powder is dissolved in water and adjusted to a pH of 7.5 with 2 N-sulfuric acid. The solution is passed through a column packed with a cation exchange resin, such as Amberlite CG-50 type I (ammonium form) (Rohm & Haas Co., USA). After washing the column with water, 0.2 N-aqueous ammonia is passed through the column. First, several minor components are eluted and then a mixture of fortimicin B and fortimicin KE is eluted as a large active fraction. Then, after several minor components are eluted, fortimicin D and fortimicin A are eluted. Active fractions containing fortimicin KE and fortimicin B are concentrated to dryness to obtain a powder of the free base of these compounds. Then the powder is subjected to silica gel column chromatography using a mixed solvent of isopropanol, chloroform and concentrated aqueous ammonia (4:2:1 by volume) as the developer. The powder is suspended in the solvent and introduced into the column. Elution is carried out with the same solvent at a flow rate of about 30 ml/hour. First, fortimicin B is eluted and then fortimicin KE is eluted. The fractions containing fortimicin KE are combined and concentrated under reduced pressure. The residue is dissolved in a small amount of water and then freeze-dried to obtain the free base of fortimicin KE.

The following Steps 1 to 5 are utilized for the chemical modifications according to the invention.

Step 1

Fortimicin KE is reacted with urethane-type acylating reagent represented by the general formula: ROCOX (wherein R is an alkyl group having 1 to 7 carbon atoms or an aralkyl group having 7 or 8 carbon atoms, and X is Cl, Br, I, N₃,

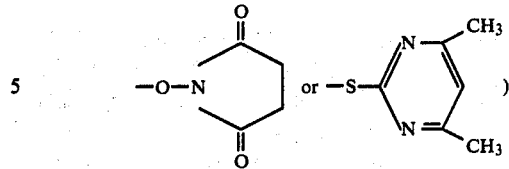

in a solvent to obtain a compound represented by the above-mentioned formula III, wherein a hydrogen atom in the amino group bonded to the carbon atom at the 6'-position of fortimicin KE is replaced by a group represented by ROCO (wherein R is the same significance as defined above).

As a urethane-type acylating reagent, compounds represented by the following formulae may be used.

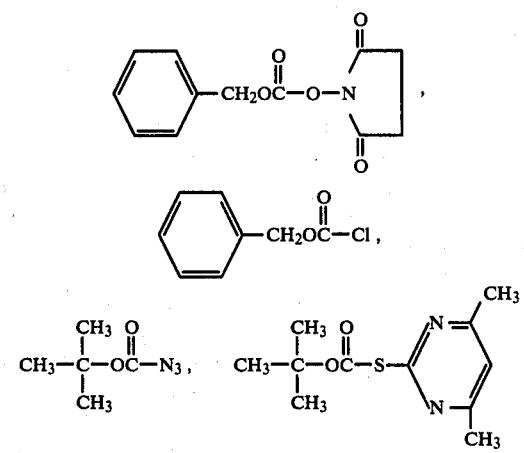

The urethane-type acylating reagent is used preferably in an amount of 1.0 to 1.2 moles per mol of fortimicin KE, and the latter compound is preferably used at a concentration of 1 to 250 mM.

Dimethylformamide, tetrahydrofuran, dioxane, methanol, ethanol, water or a mixture thereof are suitable solvents for the reaction.

The reaction is carried out at a temperature of 0° to 60° C., preferably 0° C. to room temperature for, usually, 1 to 18 hours.

The compound represented by formula III obtained in the above manner is isolated from the reaction mixture by the following way. First the reaction mixture is distilled to remove the solvent. Then water is added to the residue (1 to 10 times the weight of the residue) to extract a water-soluble portion. The extract is adjusted to a pH of 5 to 6 with an alkali or an acid and passed through a column packed with a weakly acidic cation exchange resin, for example, Amberlite CG-50 (product of Rohm & Haas Co.). After washing with water, elution is carried out with 0.01 to 1 N aqueous ammonia. Fractions containing the compound represented by formula III are combined and the aqueous ammonia is then distilled away to obtain the desired compound as a white powder. This compound may also be isolated and purified by using other known methods such as silica gel column chromatography. In the foregoing steps, presence of the compound of formula III is checked by silica gel thin layer chromatography using the lower layer of a mixed solvent of chloroform, methanol and 14% aqueous ammonia (2:1:1 by volume) as the developer.

Step 2

The compound obtained in Step 1 is reduced in a non-aqueous solvent in the presence of a reducing agent for converting the ROCO group to a methyl group at a temperature of from room temperature to the reflux temperature of the solvent to obtain the compound represented by the formula I-B, i.e., 6'-N-methylfortimicin KE.

As the solvent, tetrahydrofuran, dioxane, diethylether, or a mixture thereof is used. As the reducing agent, lithium aluminum hydride, diborane, etc. are appropriate.

The reducing agent is used in an amount of 10 to 100 moles per mol of the formula III compound and the latter is used preferably at a concentration of 1 to 100 mM. Usually, the reaction is carried out for 3 to 18 hours.

6'-N-methylfortimicin KE formed in the reaction mixture is isolated by the following way. The remaining excess of reducing agent in the reaction mixture is decomposed by adding ethylacetate or water in an amount of 10 times the reducing agent by weight and distilling away the solvent under reduced pressure. The thus obtained residue is adjusted to a pH of 5 to 6 with an acid and 10 times the residue by volume of water is added thereto to extract a water-soluble portion. The extract is passed through a column packed with a weakly acidic cation exchange resin such as Amberlite CG-50. The extract is used either as it is or as a filtrate obtained by adjusting the extract to a pH of 5 to 6 and removing the resulting precipitate by filtration. After washing the column with water, elution is carried out with 0.1 to 1 N aqueous ammonia. Fractions containing 6'-N-methylfortimicin KE are combined and the aqueous ammonia is removed under reduced pressure to obtain a white powder of 6'-N-methylfortimicin KE. The presence of 6'-N-methylfortimicin KE is checked by silica gel thin layer chromatography using the lower layer of a mixed solvent of chloroform, methanol and concentrated aqueous ammonia (1:1:1 by volume).

Step 3

6'-N-methylfortimicin KE is reacted with an amino-protecting reagent in a solvent to obtain a compound represented by formula IV wherein the amino groups at the 1, 2' and 6'-positions are protected with an amino-protecting group such as

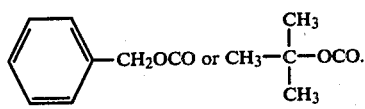

As the amino-protecting group, those usually used in the field of peptide-synthesis are appropriate. Preferably, an amino-protecting group which does not require an alkaline treatment on elimination is used because the compound represented by the formula V is unstable in an alkaline condition. As an amino-protecting agent which satisfies the requirement mentioned above, the following agents may be used.

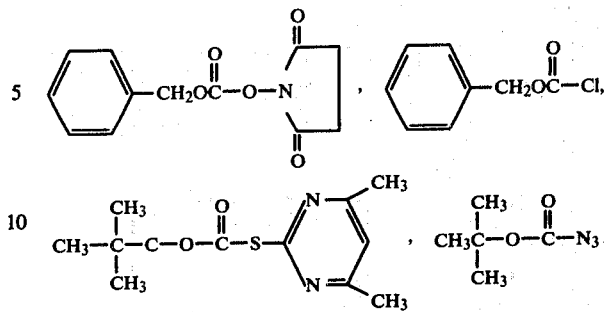

The amino-protecting agent is preferably used in an amount of 3 to 4 moles per mol of 6'-N-methylfortimicin KE. 6'-N-methylfortimicin KE in the reaction mixture is used at a concentration of 1 to 250 mM.

As a solvent, dimethylformamide, tetrahydrofuran, dioxane, methanol, ethanol, acetone, water, or a mixture thereof is used.

The reaction is carried out at a temperature of 0° to 60° C. for 2 to 24 hours.

The compound represented by formula IV synthesized in the above manner is used in the following step either as it is in the reaction mixture or after being isolated therefrom.

Isolation of the compound from the reaction mixture is carried out by the following way. The reaction mixture is distilled to remove the solvent and to obtain a residue. Then, 10 to 100 times the residue by volume of an organic solvent such as ethyl acetate or chloroform is added to obtain an extractable substance in the organic solvent. The extract is subjected to column chromatography using, for example, silica gel such as Kieselgel 60 (product of E. Merck & Co.). In the chromatography, elution is carried out using a mixed solvent such as chloroform and methanol (99:1 to 90:10, by volume) or ethyl acetate and ethanol (99:1 to 90:10, by volume). Fractions containing the desired compound are combined and concentrated to dryness to obtain a white powder. The desired compound is checked by silica gel thin layer chromatography using a mixed solvent of chloroform and methanol (9:1 by volume) as the developer.

Step 4

The compound represented by the formula V is obtained by condensing the compound represented by formula IV with an N-protected glycine represented by the formula: R'NHCH$_2$CO$_2$H in an adequate solvent.

As the N-protecting group (R') of the N-protected glycine, those usually used in peptide synthesis may be used, and the same protecting group as R$_1$ is preferably used. Similarly those condensation methods usually used in peptide synthesis may be used, and an active ester method using N-protected glycine as an active ester is preferably used. As the active ester of N-protected glycine, esters of N-protected glycine with

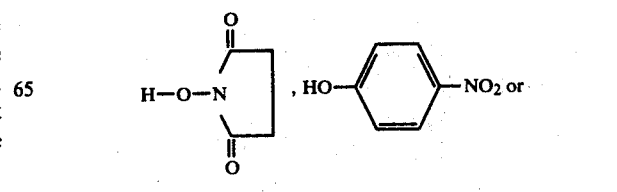

-continued

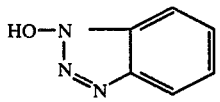

may be used, and the ester with

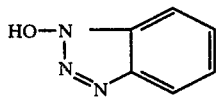

is preferably used.

The compound represented by formula IV is used at a concentration of 10 to 100 mM in the reaction mixture. Theamount of the activated derivatives at the carboxyl group in the N-protected glycine is preferably equimolar to or more than the formula IV compound. For example, when an active ester is utilized, it is used in the amount of 1 to 3 moles per mol of the compound represented by the formula IV.

Dimethylformamide, tetrahydrofuran, dioxane, chloroform, methylene chloride, or a mixture thereof are appropriate solvents.

The reaction is carried out at a temperature of $-10°$ C. to room temperature for 15 to 20 hours whereby the compound represented by formula V is formed in the reaction mixture. The compound in the reaction mixture is usually used in the following step as it is without being isolated from the reaction mixture. However, if desired, the compound may be isolated by column chromatography in the same manner as in Step 3; and its presence is checked by silica gel thin layer chromatography using a mixed solvent of chloroform and methanol (19:1 by volume) as the developer.

STEP 5

6'-N-methylfortimicin D is obtained by eliminating the amino-protecting groups, $R_1$ and $R'$ from the compound represented by formula V in a known manner. For example, when the amino-protecting group is a benzyloxycarbonyl group, the amino-protecting groups in the compound are eliminated by catalytic hydrogenation wherein hydrogen gas is contacted with the compound in a solvent such as water, tetrahydrofuran, methanol, dimethylformamide, dioxane or a mixture thereof, preferably a mixture of methanol and water (99:1 to 90:10, by volume) in the presence of a metal catalyst such as palladium-carbon, platinum and rhodium and an acid such as hydrochloric acid, acetic acid and sulfuric acid at room temperaature under atmospheric pressure. The metal catalyst is used usually in an amount of 1 to 10% (by weight) of the compound represented by the formula V. The compound represented by the formula V is used in a concentration of 10 to 100 mM. Elimination of the amino-protecting groups is completed after 2 to 18 hours.

6'-N-methylfortimicin D is isolated from the reaction mixture as an acid addition salt by filtering the catalyst away and evaporating the filtrate to dryness.

For purification, the acid addition salt is dissolved in water and passed through a column packed with a weakly acidic cation exchange resin such as Amberlite CG-50 (ammonium form) to adsorb the desired compound. After the column is washed with 5 to 10 times the resin by volume of water, elution is carried out with 0.1 to 1 N aqueous ammonia. Fractions having biological activity are combined and the solvent is distilled away to obtain a white powder of the desired compound.

The presence of the desired compound is checked by silica gel thin layer chromatography using a mixed solvent of chloroform, methanol and concentrated aqueous ammonia (1:1:1 by volume) as the developer.

6'-N-methylfortimicin D of the present invention is used as either free base or pharmaceutically acceptable acid addition salt. As the pharmaceutically acceptable acid, for example, hydrochloric acid, hydrobromic acid, hydriodic acid, sulfuric acid, amidosulfonic acid, phosphoric acid, maleic acid, acetic acid, citric acid, oxalic acid, succinic acid, benzoic acid, tartaric acid, fumaric acid, malic acid, mandelic acid and ascorbic acid may be used; and conversion of the base to an acid addition salt is accomplished by conventional processes.

Certain specific embodiments of the invention are illustrated by the following representative examples.

EXAMPLE 1

Production of 6'-N-benzyloxycarbonylfortimicin KE (Step 1)

In this example, 120 mg of fortimicin KE is dissolved in 12 ml of methanol and 89.4 mg of N-benzyloxycarbonyloxysuccinimide is added thereto with stirring. The mixture is stirred at room temperature for 2 hours. The reaction mixture is distilled under reduced pressure to remove methanol and then, 10 ml of water and 10 ml of ethyl acetate are added to the residue. The mixture is stirred vigorously and the water layer is separated therefrom. The water layer is adjusted to a pH of 6 with 1 N hydrochloric acid and passed through a column (I.D.—1 cm) packed with 25 ml of a weakly acidic cation exchange resin, Amberlite CG-50 (ammonium form) to adsorb the desired compound thereon. After washing with 100 ml of water, elution is carried out with 0.05 N aqueous ammonia and the eluate is taken in 5 ml fractions. Fraction Nos. 33 to 40 are combined and concentrated under reduced pressure to obtain 87 mg of a white powder. The powder is defined as 6'-N-benzyloxycarbonylfortimicin KE from the following properties. Yield: 47.6%

(1) In silica gel thin layer chromatography using the lower layer of a mixed solvent of chloroform, methanol and 14% aqueous ammonia (2:1:1 by volume), Rf is 0.64.

(2) NMR spectrum (methanol-$d_4$): $\delta$(ppm) 2.39 (3H, s), 3.47 (3H, s), 4.97 (1H, d), 5.07 (2H, s), 7.34 (5H, s).

(3) Mass spectrum: m/e 468 (M+), 451, 391, 305, 281, 279, 263, 235, 207, 108, 91.

(4) Melting point: 75.5° C.–78° C.

EXAMPLE 2

Production of 6'-N-methylfortimicin KE (Step 2)

In this example, 500 mg of 6'-N-benzyloxycarbonylfortimicin KE is dissolved in 30 ml of tetrahydrofuran previously dried with lithium aluminum hydride. Then, about 100 mg of lithium aluminum hydride is added to the solution and the mixture is heated under reflux and 18 hours. The reaction mixture is cooled and poured into 200 ml of ice water (0° to 5° C.) to decompose any unreacted lithium aluminum hydride. The mixture is then concentrated under reduced pressure to about 50 ml and adjusted to a pH of 6 with 1 N hydrochloric acid. The resulting precipitate is removed by filtration and the filtrate is passed through a column (I.D.—1.5 cm) packed with 50 ml of Amberlite CG-50 (ammonium form). After washing with 200 ml of water, elution is carried out with 0.2 N aqueous ammonia and the eluate is taken in 10 ml fractions. Fraction Nos. 28 to 38 are combined and aqueous ammonia is distilled away under reduced pressure to obtain 210 mg of a white powder. The powder is defined as 6'-N-methylfortimicin KE from the following properties.

Yield: 56.5%

(1) In silica gel thin layer chromatography using the lower layer of a mixed solvent of chloroform, methanol and concentrated aqueous ammonia (1:1:1 by volume), Rf is 0.72.

(2) NMR spectrum (in $D_2O$): δ(ppm) 2.38 (3H, s), 2.68 (3H, s), 3.47 (3H, s), 5.02 (1H, d).

(3) Mass spectrum: m/e 348 (M+), 331, 299, 258, 235, 217, 207, 189, 143, 114, 100, 86.

(4) Melting point: 86°–90° C.

| Elementary analysis $C_{15}H_{32}N_4O_5 \cdot CO_2$ | | |
|---|---|---|
| | Found | Calculated |
| H | 8.52% | 8.22% |
| C | 48.85 | 48.97 |
| N | 14.49 | 14.28 |

EXAMPLE 3

Production of 1,2',6'-N-tribenzyloxycarbonyl-6'-N-methylfortimicin KE (Step 3)

In this example, 220 mg of 6'-N-methylfortimicin KE is dissolved in 15 ml of methanol. Then, 10 ml of methanol solution containing 520 mg of N-benzyloxycarbonyloxysuccinimide is added in drops to the mixture with stirring. The mixture is stirred at room temperature for 18 hours. Thereafter, the reaction mixture is distilled to remove ethanol and 50 ml of ethyl acetate is added to the residue. The mixture is then washed with 50 ml of water.

The resultant ethyl acetate layer is dried with anhydrous sodium sulfate and distilled to remove the solvent whereby a crude powder of the desired compound is obtained.

For further purification, the crude powder is dissolved in 2 ml of chloroform and passed through a column (I.D.—1.5 cm) packed with 20 g of Kieselgel 60 (silica gel produced by E. Merck & Co.). Elution is carried out with a mixed solvent of methanol and chloroform (1:49, by volume). The eluate is taken in 10 ml fractions. Fraction Nos. 20 to 52 are combined and concentrated to dryness to obtain 350 mg of a white powder. The powder is defined as 1,2',6'-N-tribenzyloxycarbonyl-6'-N-methylfortimicin KE from the following properties. Yield: 71.7%

(1) In silica gel thin layer chromatography using a mixed solvent of chloroform and methanol (9:1 by volume) as the developer, Rf is 0.60.

(2) NMR spectrum (methanol-$d_4$): δ(ppm) 2.35 (3H, s), 2.87 (3H, s), 3.46 (3H, s), 5.08 (6H, s), 7.32 (15H, s).

(3) Melting point: 74° C.–76° C.

EXAMPLE 4

Production of 6'-N-methyl-N-tetrabenzyloxycarbonylfortimicin D (Step 4)

In this example, 134 mg of N-benzyloxycarbonylglycine and 86 mg of 1-hydroxybenztriazole are dissolved in 16 ml of tetrahydrofuran and 143 mg of N,N'-dicyclohexylcarbodiimide is added thereto. The mixture is stirred under cooling at a temperature of 0° to 5° C. for one hour and then 400 mg of 1,2',6'-N-tribenzyloxycarbonyl-6'-N-methylfortimicin KE is added thereto. The mixture is stirred at room temperature for 18 hours. After the precipitated impurities are removed by filtration, the filtrate is concentrated to dryness under reduced pressure to obtain a pale yellow powder. For further purification, the powder is dissolved in 2 ml of chloroform and passed through a column (I.D.—1.5 cm) packed with 20 g of Kieselgel 60 (silica gel produced by E. Merck & Co.). Elution is carried out with a mixed solvent of chloroform and methanol (1:99 by volume). The eluate is taken in 10 fractions. Fraction Nos. 20 to 31 are combined and the solvent is distilled away to obtain 310 mg of a white powder which is defined as 6'-N-methyl-N-tetrabenzyloxycarbonylfortimicin D. Yield: 61.8% The white powder has the following properties.

(1) In silica gel thin layer chromatography using a mixed solvent of chloroform and methanol (19:1 by volume) as the developer, Rf is 0.40.

(2) Melting point: 81.5° C.–84° C.

EXAMPLE 5

Production of 6'-N-methylfortimicin D (Step 5)

In this example, 310 mg of 6'-N-methyl-N-tetrabenzyloxycarbonylfortimicin D obtained in Example 4 is dissolved in 20 ml of 0.2 N HCl-methanol solution and about 40 mg of 10% palladium-carbon is added thereto. The mixture is subjected to hydrogenolysis at an ambient temperature under atmospheric pressure for 3 hours. After the catalyst is removed and the solvent is distilled away, the residue is dissolved in 5 ml of water. The solution is then passed through a column (I.D.—1 cm) packed with 10 ml of Amberlite CG-50 (ammonium form). After washing the column with 20 ml of water, elution is carried out with 0.3 N aqueous ammonia. The eluate is taken in 5 ml fractions. Fraction Nos. 13 to 18 are combined and the aqueous ammonia is distilled away to obtain 120 mg of purified 6'-N-methylfortimicin D (free base). Yield: 89.9%

Then, 100 mg of the free base of 6'-N-methylfortimicin D is dissolved in 1 ml of water and the solution is adjusted to a pH of 3 with sulfuric acid. The solution is added in drops to 20 ml of ethanol. The resulting precipitate corresponding to 130 mg of the sulfate of 6'-N-methylfortimicin D is obtained by filtration.

(1) In silica gel thin layer chromatography using the lower layer of a mixed solvent of chloroform, methanol and concentrated aqueous ammonia (1:1:1 by volume) as the developer, Rf is 0.47.

(2) NMR spectrum (proton) δ(ppm)
  a. Free base (in $D_2O$): 2.31 (3H, s), 3.02 (3H, s), 3.40 (3H, s), 3.47 (3H, s), 4.75 (1H, d).
  b. Hydrochloride (the sample wherein DCl is added to the free base to make pD=1 is used.): 2.77 (3H, s), 3.12 (3H, s), 3.47 (3H, s), 4.06 (2H, s), 5.32 (1H, d).

(3) Mass spectrum (m/e): 405 (M+), 387, 356, 292, 274, 264, 246, 207, 143.

(4) Specific rotation (sulfate form); $[\alpha]_D^{22} = +82.0°$ (c=0.2, $H_2O$).

(5) Melting point (free base): 88°–91° C.

(6) CMR spectrum is shown in FIGS. 1 and 2. FIG. 1 relates to the free base and FIG. 2 to the hydrochloride (the sample wherein DCl is added to the free base to make pD=1 is used).

| Elementary analysis $C_{17}H_{35}N_5O_6 \cdot \frac{1}{2}H_2O$ | | |
|---|---|---|
| | Found | Calculated |
| H | 8.79% | 8.75% |
| C | 49.00 | 49.26 |
| N | 16.63 | 16.89 |

What is claimed is:

1. A composition of matter represented by the formula

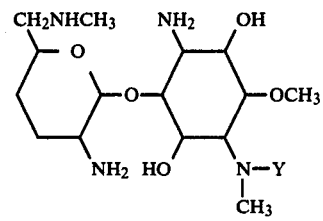

wherein Y is H or $COCH_2NH_2$.

2. A composition of matter according to claim 1 wherein Y is H, said composition being 6'-N-methylfortimicin KE.

3. A composition of matter according to claim 1 wherein Y is $COCH_2NH_2$, said composition being 6'-N-methylfortimicin D.

4. 6'-N-methylfortimicin D and the pharmaceutically acceptable non-toxic acid addition salts thereof.

* * * * *

UNITED STATES PATENT AND TRADEMARK OFFICE
CERTIFICATE OF CORRECTION

PATENT NO. : 4,169,942
DATED : October 2, 1979
INVENTOR(S) : Kenichi Mochida, et al.

It is certified that error appears in the above-identified patent and that said Letters Patent are hereby corrected as shown below:

Col. 2, lines 30 to 40, the formula for Compound (1-A) should be:

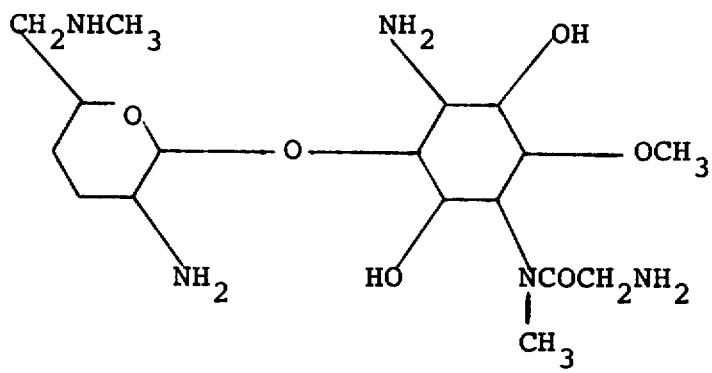

Col. 4, line 10, "$C_{17}H_{35}N_5O_6 6.20$" should be --$C_{17}H_{35}N_5O_6 \cdot \frac{1}{2}H_2O$--

Col. 4, Table 1, the 6th entry under "Microorganisms" should read:

--Escherichia coli 3100        6.25        6.25        3.12--

Col. 4, Table 1, "Escherichi coli 76-2*1" should read --Escherichia coli 76-2*1--;

Col. 9, line 51, "temperaature" should be --temperature--;

UNITED STATES PATENT AND TRADEMARK OFFICE
CERTIFICATE OF CORRECTION

PATENT NO. : 4,169,942
DATED : October 2, 1979
INVENTOR(S) : Kenichi Mochida, et al.

It is certified that error appears in the above-identified patent and that said Letters Patent are hereby corrected as shown below:

Col. 10, line 61, "and" (second occurrence) should be --for--;

Col. 11, line 38, "ethanol" should be --methanol--;

Col. 11, line 52, "350" should be --340--;

Col. 12, line 15, after "10" add --ml--.

Signed and Sealed this

Eleventh Day of December 1979

[SEAL]

Attest:

SIDNEY A. DIAMOND

Attesting Officer

Commissioner of Patents and Trademarks